United States Patent [19]

Risley

[11] Patent Number: 4,929,542
[45] Date of Patent: May 29, 1990

[54] IN VITRO SCREENING TEST FOR MUTAGENICITY AND GENOTOXICITY DURING SPERMATOGENESIS

[75] Inventor: Michael S. Risley, City Island, N.Y.

[73] Assignee: Cornell Research Foundation, Inc., Ithaca, N.Y.

[21] Appl. No.: 114,986

[22] Filed: Oct. 30, 1987

[51] Int. Cl.$^5$ .................. A01N 1/02; C12Q 1/00; C12Q 1/02; C12N 5/00

[52] U.S. Cl. ............................ 435/2; 435/4; 435/29; 435/240.3; 435/240.31; 435/243; 435/244; 435/809

[58] Field of Search ............ 435/2, 4, 29, 41, 240.3, 435/240.31, 244, 245, 820, 240.1, 76, 30, 243, 809

[56] References Cited

PUBLICATIONS

Hollinger et al, Gamete Research, vol. 3, 1980, pp. 45–57.
Muller et al, General and Comparative Endocrinology, vol. 42, 1980, pp. 365–377.
Kalt, J. Exp. Zool., vol. 195, 1976, pp. 393–408.
Steinberger, Endocrinology, vol. 74, 1964, pp. 788–792.
Risley et al, Chromosoma, vol. 94(3), 1986, pp. 217–227.
Skare et al, Mutation Research, vol. 130, 1984, pp. 295–303.
Lähdetie, Mutation Research, vol. 120, 1983, pp. 257–260.
Parvinen et al, Endocrinology, vol. 112, No. 3, 1983, pp. 1150–1152.
Risley et al, Biological Abstracts, Abstract No. 44589, 1979.
Risley et al, Biological Abstracts, Abstract No. 23693, 1987.
Risley et al, Biological Abstracts, vol. 84, Abstract No. 103210, 1987.
Sega et al, "Environmental Mutagenesis", Official Journal of the Environmental Mutagen Society, vol. 4, No. 3, pp. 347–348, 1982.
M. Parvinen, W. W. Wright, D. M. Phillips, J. P. Mather, N. A. Musto, C. W. Bardin, "Spermatogensis In Vitro: Completion of Meiosis & Early Spermiogensis", Endocrinology 0013-7227/83/1123-1150.
A. Steinberger, "In Vitro Techniques for the Study of Spermatogenesis", Metl. Enz., vol. 39, PI.D, AC. Press N.Y. (1975), pp. 283–297.
J. Toppari & M. Parvinen, "In Vitro Differentiation of Rat Seminiferous Tubular Segments from Defined Stages of the Epithelial Cycle Morphologic & Immunolocalization Analysis", Journal of Andrology Nov./Dec. 1985, vol. 6, pp. 334–343.
A. Steinberger & E. Steinberger, "Differentiation of Rat Seminiferous Epithelium in Organ Culture", F. Reprod. Fertil. (1965), 9, 243–248.
L. L. Tres and A. L. Kierszenbaum, "Viability of Rat Spermatogenic Cells In Vitro is Facilitated by Their Coculture with Sertoli Cells in Serum–Free Hormone–Supplemented Medium", Proc. Nat'l Acad Sci. USA, vol. 80, pp. 3377–3381 (Jun. 1983).

(List continued on next page.)

*Primary Examiner*—David M. Naff
*Assistant Examiner*—Florina B. Hoffer
*Attorney, Agent, or Firm*—Sughrue, Mion, Zinn, Macpeak & Seas

[57] ABSTRACT

An in vitro screening test for identifying mutagenic and genotoxic agents during spermatogenesis, comprising: (1) Culturing Xenopus testis explants in vitro in the presence of one or more suspected mutagenic and/or genotoxic agent(s); (2) Removing said one or more suspected agent(s) and continue culturing said Xenopus testis explants such that spermatogonia in said Xenopus testis explants undergo spermatogenesis; (3) Isolating sperm and/or one or more types of spermatogenic cells at various times during step (2); and (4) Determining the mutagenic and/or genotoxic affect of said agent(s). A novel medium suitable for culturing Xenopus testis explants. A novel method for culturing Xenopus testis explants in vitro such that cells at all stages of the spermatogenic cycle are produced comprising culturing Xenopus tests fragments in the novel medium under an atmosphere of air and at a temperature in a range of from about 20° C. to about 24° C.

12 Claims, 4 Drawing Sheets

OTHER PUBLICATIONS

Michael S. Risley, Spermatogenic Cell Differentiation In Vitro, Gamete Research 4:331–346 (1983).

M. Risley & R. Eckhardt, Dissociation & Separation of Xenopus Laevis Spermatogenic Cells, Reprint, "The Journal of Experimental Zoology" (vol. 207, No. 1, Jan. 1979), pp. 93–105.

M. Risley, A. Miller, D. Bumcrot, In Vitro Maintenance of Spermatogenesis in Xenopus Laevis Testis Explants Cultured in Serum-Free Media, Biology of Reproduction 36, 985–997 (1987).

Lahdetie, J., "Meiotic Micronuclei Induced by Adriamycin in Male Rats", Mutation Research 119 (1983), 79–82.

Lahdetie, J. "Micronuclei Induced During Meiosis by Ethyl Methanesulfonate, Cyclophosphamide and Dimethylbenzanthracene in Male Rats", Mutation Research, 120 (1983), 257–260.

Sega, G. A., "Unscheduled DNA Synthesis (DNA Repair) in the Germ Cells of Male Mice-Its Role in the Study of Mammalian Mutageneis", Genetics 92, 49'4 58 (1979).

Sega, G. A., Sluder, A. E., McCoy, L. S., Owens, J. G. and Generoso, E. E., "The Use of Alkaline Elution Procedures to Measure DNA Damage in Spermiogenic Stages of Mice Exposed to Methyl Methanesulfonate", Mutation Research, 159 (1986), 55–63.

Risley, M. S., "Spermatogenic Cell Differentiation In Vitro", Gamete Research 4:331–346 (1983).

Abe, Shin-Ichi, "Meiosis of Primary Spermatocytes and Early Spermiogenesis in the Resultant Spermatids in Newt, Cynops Pyrrhogaster In Vitro", Differentiation, 20, 65–70, 1981.

Risley, M. S., and Eckhardt, R. A., "Evidence for the Continuation of Meiosis and Spermiogenesis in In Vitro Cultures of Spermatogenic Cells from Xenopus Laevis" (1979), J. Exp. Zool., 207:513–520.

Nishikawa A., and Abe, Shin-Ichi, "Progression Throughout all Stages of Meiosis from the Early Prophase of Newt Primary Spermatocytes In Vitro", Develop. Growth and Differ. 25(3), 323–331 (1983).

Risley, M. S. "Spermatogenic Cell Differentiation In Vitro", Gamete Research 4:331–346 (1983).

Fell, H. F., "Recent Advances in Organ Culture", Science Progress 41 (162): 212–231 (1953).

Trowell, O. A., "the Culture of Mature Organs in a Synthetic Medium", Experimental Cell Research 16, 118–147 (1959).

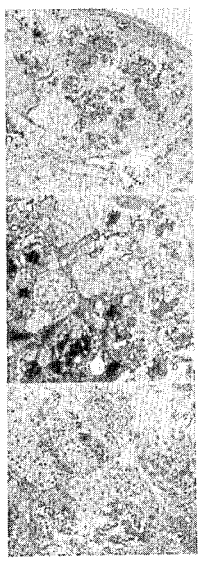
FIG.1a
FIG.1b
FIG.1c
FIG.2a  FIG.2b
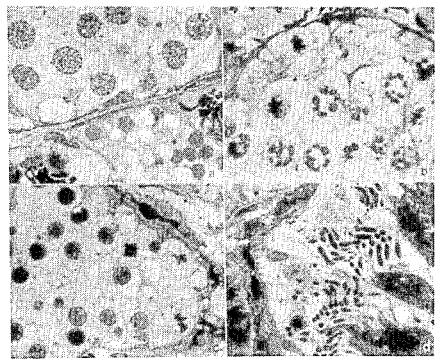
FIG.2c  FIG.2d

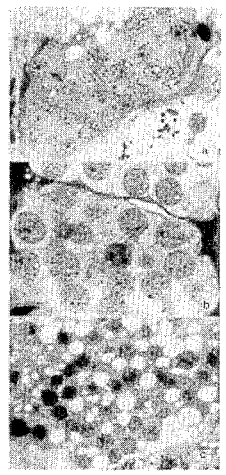
FIG. 3a
FIG. 3b
FIG. 3c
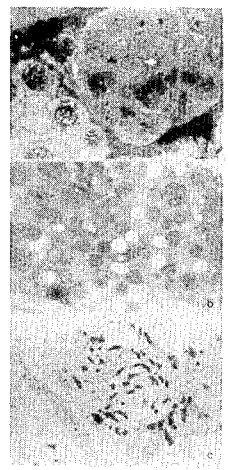
FIG. 4a
FIG. 4b
FIG. 4c

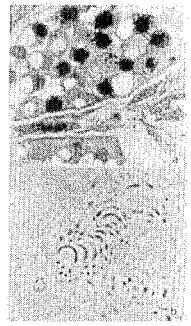
FIG.5a
FIG.5b
FIG.6

IN VITRO SCREENING TEST FOR MUTAGENICITY AND GENOTOXICITY DURING SPERMATOGENESIS

This work was supported by grant number ES 03381 from the National Institute of Environmental Health Sciences.

FIELD OF THE INVENTION

The present invention relates to a screening test for mutagenicity and genotoxicity during spermatogenesis. In particular, the present invention relates to an in vitro screening test for mutagenicity and/or genotoxicity during spermatogenesis. The screening test can be used to concurrently test multiple genetic endpoints.

The present invention also relates to a novel medium for culturing Xenopus testis explants used in the in vitro assay and to a novel method for culturing Xenopus testis explants in vitro such that cells at all stages of the spermatogenic cycle are produced.

BACKGROUND OF THE INVENTION

Chemicals or environmental factors which may increase the frequency of heritable germ cell mutations, particularly chromosome aberrations. represent significant hazards to human health. Mutagenic and genotoxic agents released into the environment also represent significant hazards to the economic well being of humans since they can have severe negative effects on the reproduction and long term survival of a variety of economically important plant and animal species.

Genomic aberrations acquired by developing and mature germ cells may contribute to sterility, fetal death, congenital abnormalities or metabolic disorders. Chemical agents and environmental agents that may induce genomic aberrations in developing gametes therefore represent significant hazards to the health and reproduction of humans and other animal species and should be screened routinely for this capacity; however, few such agents have been evaluated adequately.

A variety of in vivo and in vitro assays have been developed to evaluate mutagenic and/or genotoxic agents in somatic cells, but with few exceptions most are not adequate to assess the ability of the agents to induce chromosome aberrations in developing germ cells, especially in the male germ line. Vertebrate spermatogenesis is a complex pathway of cellular differentiation comprised of a mitotic phase of stem cell (spermotogonia) proliferation, followed by a unique premeiotic S phase, meiosis, and spermatid maturation. Due to unique characteristics of each phase, it may be expected that they will vary in their sensitivities to different mutagenic and genotoxic agents. The frequency of induction of dominant lethals and heritable translocations is indeed stage specific.

Clearly, the potential of mutagenic and genotoxic agents to induce heritable chromosome aberrations in the male germ line should be evaluated in male germ line genotoxicity and heritable mutation assays. The most appropriate testing procedures currently used are the in vivo mammalian germ cell heritable mutation assays, such as the mouse specific locus test (W. L. Russell, 1951. *Cold Spring Harbor Symp. Quant. Biol.* 16:327-336: L. B. Russel et al., 1981. *Mutat. Res.* 86:329-354). the rodent dominant lethal assay (V. H. Ehling et al., 1978, *Arch. Toxicol.* 39:173-185; Green et al., 1985, *Mutat. Res.* 154:49-67), and the heritable translocation test (Generoso et al., 1980. *Mutat. Res.* 76:191-215; Leonard. A. and Adler, I. D., 1984. In "Handbook of Mutagenicity Test Procedures" (Kilbey et al., eds.) Elsevier, pp. 485-494).

The specific locus and heritable translocation tests are essential for risk estimation in mammals since they are in vivo tests that measure heritable mutations which represent direct health hazards. Due to the requirements for large numbers of animals and extensive facilities however, the in vivo tests are prohibitively expensive, tedious and time consuming. For example, the fastest and least expensive mammalian heritable mutation assay (dominant lethal test) ranges in cost between $15,000 and $20.000 and requires 10 to 12 weeks for a nonduplicated test. This test is also the least sensitive in vivo assay. A mouse specific locus test may cost more than $100.000 (for a review of test costs, see D. Brusick and A. Auletta, 1985, *Mutation Research* 153:110).

Given the number of mutagenic and genotoxic agents and the variety of concentrations that should be tested, it is not realistic to expect routine evaluation by the heritable mutation assays. Such in vivo assays also suffer a lack of sensitivity; test agents often must be applied in doses that cause a generalized toxicity that may indirectly result in germ line genotoxicity.

Drosophila heritable mutation assays are rapid and economical, and they are capable of measuring multiple genetic endpoints (Wurgler. F. E. et al., 1984. In "Handbook of Mutagenicity Test Procedures" (B. J., Kilbey et al., eds.) Elsevier, pp. 555-601). Male meiosis in Drosophila, however, is atypical since synaptonemal complexes do not form, and homologous chromosomes do not recombine and form chiasmata. Spermatogenesis in Drosophila, moreover, is physiologically distant from that in vertebrates as evidenced by the short time (8-10 days) required for sperm development.

Another approach to screening chemicals as potential inducers of heritable mutations is to employ the less costly and more rapid in vivo mammalian germ cell genotoxicity assays. These assays include cytogenetics of spermatogonial and spermatocyte chromosomes, spermatid micronucleus assays (Lähdetie,. J., 1983 *Mutat. Res.* 119:79-82 and 120:257-260). unscheduled DNA synthesis (UDS) assays (Sega. G. A., 1979. *Genetics* 92:549-558), and alkaline elution assays for DNA breaks in spermatogenic cells (Sega. G. A. and Owens, J. G., 1982. *Environ. Mutagen* 4:347-348: Sega. G. A. et al., 1986, *Mutat. Res.* 159:55-63). Since each of these assays follows in vivo protocols, they suffer some of the drawbacks of the heritable mutation assays. These assays are also incapable of estimating the frequency of specific chromosome aberrations that appear in functional sperm and thus represent significant health hazards.

In vitro screening tests that could identify agents as candidates for further risk assessment in in vivo mammalian assays would be valuable additions to a testing program for germ cell mutagenicity and genotoxicity. Ideally, such tests would employ sperm and spermatogenic cells, permit evaluation of a wide range of test agent concentrations, be highly sensitive to a variety of test agents, and be cost effective.

Progress towards developing in vitro assays has been hindered in part by an inability to maintain spermotogenesis in vitro. Isolated mammalian spermatogenic cells rapidly degenerate in cell culture, and only limited development of mammalian spermatogonia and spermatocytes through meiotic prophase has been maintained in vitro in testis organ cultures (Steinberger and Steinberger, 1965, *J. Repro. Fertil.* 9:243-248: Steinberger. 1975, Hardman J. G., O'Malley B. W. (eds). *Methods in Enzymology*, New York: Academic Press, 283-296) and spermatogenic cell-Sertoli cell co-cultures (Tres and Kierszenbaum, 1983, *Proc. Nat'l Acad. Sci. USA* 80:3377-3381). Development from pachytene to round spermatid stages has been achieved recently in 7 day cultures of rat seminiferous tubules (Parvinen et al., 1983, *Endocrinology* 112:1150-1152; Toppari and Parvinen, 1985. *J. Androl.* 6:334-343) but in vitro development of mammalian spermatogenic cells beyond the round spermatid stage has not been observed.

Spermatogenic cells from amphibians and insects can be maintained in vitro more readily than their mammalian counterparts. In cell cultures, isolated spermatocytes from the frog *Xenopus laevis* develop from meiotic prophase to elongate spermatid stages (Risley and Eckhardt, 1979, *J. Exp. Zool.* 207:513-520; Risley, 1983, *Gam Res.* 4:331-346), and spermatocytes from the newt Cynops pyrrhogaster develop from early meiotic prophase to the round spermatid stage (Abe. 1981, *Differentiation* 20:65-70); Nishikawa and Abe, 1983, *Develop. Growth. Differ.* 25:232-331). Development from primary spermatocyte stages to late spermatid stages has also been observed in cultured testes from silkworms (Kambysellis and Williams, 1972, *Science* 175:769-770) and in cultured testes (Fowler GL. 1973, Cell. Differ. 2:33-42) and spermatocysts from Drosophila (Cross and Shellenbarger, 1979 *J. Embryol. Exp. Morphol.* 53:345-351; Liebrich, 1981, *Cell Tissue Res.* 220:251-262). Despite the advanced in vitro differentiation obtained with amphibian and insect spermatogenic cells, development of spermatogonia to postmeiotic stages and differentiation of sperm have not been observed in culture.

Many of the disadvantages in current screening tests could be circumvented by the development of an in vitro mutagenicity and genotoxicity test that assays most spermatogenic stages in a vertebrate. The capability to assay multiple genetic endpoints would also be advantageous. In vitro germ line screening tests have not been developed to date since an animal model for in vitro spermatogenesis was not available.

SUMMARY OF THE INVENTION

Accordingly, one object of the present invention is to provide an in vitro germ line mutagenicity and genotoxicity test for spermatogenesis.

A second object of the present invention is to provide a screening test for mutagenicity and genotoxicity during spermatogenesis that permits direct exposure of the testes to a wide range of concentrations of the test agent, thus maximizing sensitivity.

A third object of the present invention is to provide a screening test for mutagenicity and genotoxicity during spermatogenesis, wherein the frequency of induction of aberrations can be measured in vitro throughout the spermatogenic cycle.

A fourth object of the present invention is to provide a screening test for mutagenicity and genotoxicity during spermatogenesis, wherein the survival of aberrations from one stage to another may be determined.

A fifth object of the present invention is to provide a screening test for mutagenicity and genotoxicity during spermatogenesis, wherein relatively few animals are required.

A sixth object of the present invention is to provide a screening test for mutagenicity and genotoxicity during spermatogenesis, wherein live animals are not exposed to pain and suffering.

A seventh object of the present invention is to provide a screening test for mutagenicity and genotoxicity during spermatogenesis, wherein a vertebrate species is used that has a similar genome size to that in mammals, and a similar timing of spermatogenesis to that in mice.

An eighth object of the present invention is to provide a screening test for mutagenicity and genotoxicity during spermatogenesis, wherein direct contact between the testes and a test agent can be controlled, both quantitatively and temporally.

A tenth object of the present invention is to provide a screening test for mutagenicity and genotoxicity during spermatogenesis, wherein the opportunity for , endogenous cellular metabolic activation of indirect mutagens is maintained.

An eleventh object of the present invention is to provide a screening test for mutagenicity and genotoxicity during spermatogenesis that is relatively fast.

A twelfth object of the present invention is to provide a screening test for mutagenicity and genotoxicity during spermatogenesis that will permit in vitro analysis of pharmacological approaches to the protection of germ cells from mutagens.

A thirteenth object of the present invention is to provide a novel medium suitable for culturing Xenopus testis explants.

A fourteenth object of the present invention is to provide a method for culturing Xenopus testis explants in vitro such that cells at all stages of the spermatogenic cycle are produced.

These and other objects have been attained by providing an in vitro screening test for identifying mutagenic and genotoxic agents during spermatogenesis, comprising: (1) Culturing Xenopus testis explants in vitro in the presence of one or more suspected mutagenic and/or genotoxic agent(s); (2) Culturing the Xenopus testis explants from step (1) in the absence of the one or more suspected agent(s) such that spermatogonia in the Xenopus testis explants undergo spermatogenesis; (3) Isolating sperm and/or one or more types of spermatogenic cells at various times during step (2); and (4) Determining the mutagenic and/or genotoxic affect of the agent(s). In a preferred embodiment the screening test is used to concurrently test multiple genetic endpoints.

A novel medium suitable for culturing Xenopus testis explants used in the in vitro assay is also provided.

Additionally, there is provided a method for culturing Xenopus testis explants in vitro such that cells at all stages of a spermatogenic cycle are produced, comprising culturing Xenopus testis fragments in the above-referred to novel medium under an atmosphere of air and at a temperature of about 20° to 24° C.

BRIEF DESCRIPTION OF THE DRAWINGS

FIG. 1 shows photomicrographs of toluidine blue stained sections from control testes (a) and testis fragments cultured 14 days (b) and 28 days (c). X 260.

FIG. 2 shows photomicrographs of spermatogenic stages in testis fragments cultured 28 days. a, pachytene spermatocytes (top cyst) and acrosomal vesicle stage spermatids (bottom cyst); arrowhead indicates the acrosome vesicle; arrow indicates a follicle cell. b, cyst with late diplotene through metaphase I spermatocytes. c, cyst with secondary spermatocytes, some of which are at metaphase II (arrow). d, mature spermatids (large arrow) embedded in Sertoli cell (small arrow); lobule boundary cells indicated by arrowhead. X 1400.

FIG. 3 shows autoradiographs of sections from testis fragments incubated in media containing $^3$H-thymidine and cultured for 14 and 28 days. a, labelled secondary (type B) spermatogonia from day 1. b, labelled zygotene spermatocytes (arrow) and unlabelled pachytene spermatocytes in testes cultured 14 days. c, labelled acrosomal vesicle stage spermatids in testis fragments cultured 28 days. X 1400.

FIG. 4 shows autoradiographs of sections from testis fragments of a frog injected with $^3$H-thymidine 15 days prior to dissection and subsequent culture for 14 and 28 days. a, labelled zygotene spermatocytes (arrow) and unlabelled pachytene spermatocytes from freshly dissected testis fragments. b, labelled acrosomal vesicle stage spermatids from explants cultured 14 days. c, labelled nuclei of mature spermatids in explants cultured 28 days; phase contrast photomicrograph of an unstained section to enhance contrast between the silver grains and dense sperm nuclei. X 1400.

FIG. 5 shows autoradiographs of sections from testis fragments incubated with $^3$H-thymidine and cultured 28 and 35 days in serum-free XSCM medium 2. a, labelled acrosomal vesicle stage spermatids from explants cultured 28 days. b, labelled nuclei of mature spermatids in explants cultured 35 days: slightly defocussed phase contrast photomicrograph of an unstained section. X 1400.

FIG. 6 is a phase contrast photomicrograph of Xenopus round spermatids with developing acrosomal vesicles (av). X 3200.

DETAILED DESCRIPTION OF THE INVENTION

Figure 7:
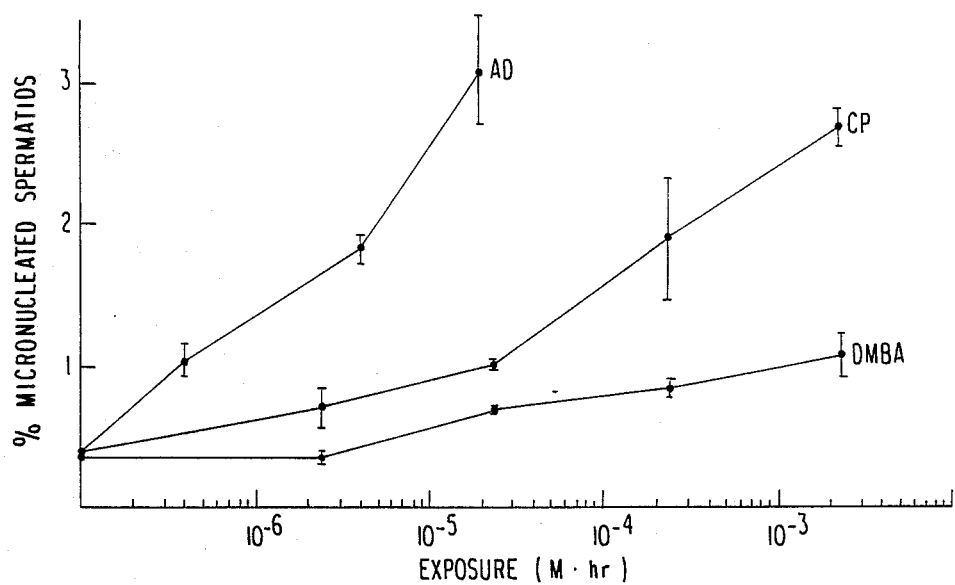
FIG. 7 is a graphic representation of the percent of round spermatids with micronuclei present in testis explants incubated with cyclophosphamide (CP). 9,10-dimethyl-1,2-benzanthracene (DMBA) or adriamycin (AD) and cultured 30 days. Exposure is defined as the product of mutagen concentration (moles/L) and time of exposure (hr). The data were obtained from Tables 1 (CP), 3 (DMBA) and 6 (AD) in the Examples. The data points which lie on the Y-axis correspond to the micronucleus counts in control cultures.

According to the present invention, spermatogenesis between late spermatogonial and mature spermatid stages can be maintained for extended periods (about 28 days) and fertile sperm can also be produced from spermatogonia in cultured (35 days) testis explants from the frog of the genus Xenopus. These cultures can be used to screen one or more agents for mutagenicitY and/or genotoxicity. Further, the cultured testis explants can be used to detect agents that act directly or that require metabolic activation.

The fact that use of testis fragments for in vitro assays also maintains the mechanisms for metabolic activation of indirect mutagens or genotoxins is an important consideration for in vitro assays since false negative tests could result from failure to form the ultimate mutagenic or genotoxic agent in vitro.

This in vitro culture system is particularly suitable for the screening test of the present invention because the overall kinetics of spermatogenesis in Xenopus (Kalt. 1976, J. Exp. Zool. 195:393-408) is similar to that for several mammals; the genome size and, thus, the target size/cell for mutagenic and genotoxic agents is comparable in Xenopus (3.2 pg/haploid genome: Dawid, 1965, J. Mol. Biol. 12:581-599) and mammals (3-3.3 pg/haploid genome); and unlike many other submammalian species, spermatogenesis in Xenopus is continuous, even under laboratory conditions. In addition, spermatogenesis in Xenopus is an excellent model of this process in a variety of cold-blooded organisms.

DEFINITIONS OF TERMS

For purposes of this application, the following terms have the definitions set forth below.

Mutagenicity -- Having the capability to cause DNA rearrangments in germ cells that will be inherited by offspring.

Genotoxicity -- Having the capability to cause DNA rearrangments in germ cells that may or may not be inherited by offspring: heritability is not known.

Mutagenic agent -- Any chemical or physical item capable of inducing heritable DNA damage in germ cells.

Genotoxic agent -- Any chemical or physical item capable of inducing DNA rearrangements, either transient or permanent, in germ cells; heritability is not known.

Clastogenesis -- The breakage or numerical rearrangement of chromosomes.

Spermatogenesis -- The process by which cells develop into sperm. The process consists of three major phases: 1. Mitotic Phase - stem cells divide 4 to 6 times to produce a pool of spermatogonia which are committed to develop into sperm. The stem cells also renew themselves. 2. Meiotic Phase - after a final phase of DNA replication (premeiotic S phase) primary spermatocytes are produced which carry out the unique functions of chromosome pairing and DNA recombination. The phase ends with two meiotic cell divisions. The first division separates homologous chromosomes and produces secondary spermatocytes. In the second division, the secondary spermatocytes each produce two haploid round spermatids. 3. Spermiogenic Phase - without further division the round spermatids develop into sperm by forming an acrosome and flagellum, shedding excess cytoplasm and condensing and shaping the nucleus in a species-specific manner.

Spermatogonia -- Mitotically active stem cells to the process of spermatogenesis.

Primary spermatogonia: Type A Spermatogenia -- The first spermatogonial stage which initiates spermatogenesis.

Secondary Spermatogonia; Late Spermatogonia; Type B Spermatogonia -- A population of mitotically active cells which develop from primary (or Type A) spermatogonia.

Spermatocyte -- The cell types which develop after spermatogonia but before spermatids.

Premeiotic S Spermatocyte -- Spermatocytes engaged in the final period of DNA replication during spermatogenesis.

Primary Spermatocyte -- A tetraploid (4C) cell which develops from Type B (secondary) spermatogonia and carries out the processes of meiotic prophase.

Preleptotene Spermatocyte -- Early primary spermatocyte stage preceding leptotene and active in DNA replication.

Leptotene spermatocyte -- Primary spermatocyte stage during which homologous chromosomes prepare to pair with each other.

Zygotene spermatocyte - Primary spermatocyte stage during which homologous chromosomes begin and complete pairing.

Pachytene spermatocyte -- Primary spermatocyte stage during which paired homologous chromosomes cross-over (exchange DNA segments).

Diplotene Spermatocyte - Primary spermatocyte stage during which homologous chromosomes unpair except at points (chiasma) where they have crossed-over (exchanged DNA segments).

Diakinesis Spermatocytes - Stage during which homologous chromosomes have completed unpairing and have become condensed in preparation for the first meiotic division.

Secondary Spermatocyte -- Diploid (2C) cells produced by meiotic division of primary spermatocytes.

Spermatid -- Haploid (1C) cells produced by meiotic division of secondary spermatocytes; these cells develop into sperm without dividing.

Figure 8:
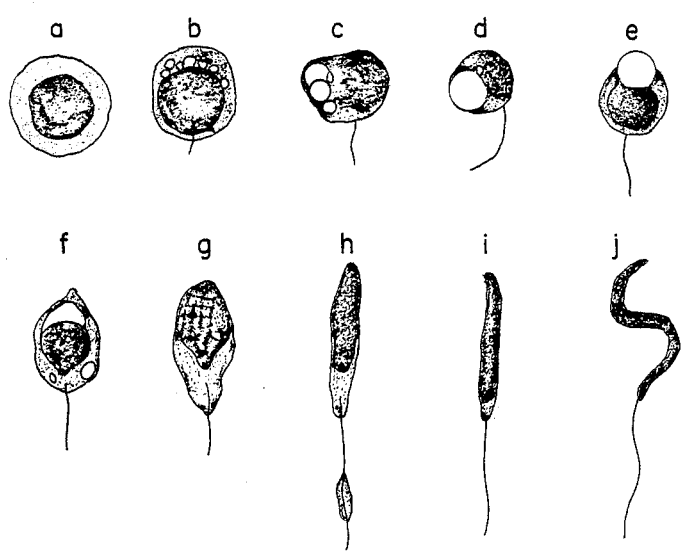
FIG. 8 is a diagram illustrating the process of growth and change a spermatid undergoes to become functional sperm: a, b, c, early spermatid; d, e, f, mid-spermatid; f, g, mid-late spermatid; g, h, i, late spermatid; j, mature spermatid. Also, a to e, round spermatid; c to f, acrosome vesicle stage round spermatids.

Early spermatid -- Round spermatid with initial stages of acrosome development and flagellar development (see FIG. 8, a, b and c).

Mid-spermatid -- Spermatid with prominent acrosome and developed flagellum (see FIG. 8, d, e, f).

Mid-late spermatid -- Mixture of mid and late spermatids with those shown in FIG. 8, f and g predominant.

Late spermatid -- Spermatid with acrosome condensed, nucleus elongating, cytoplasm moving posteriorly and being shed (see FIG. 8, g, h and i).

Mature spermatid -- Spermatid with nucleus fully helical, chromatin condensed, cytoplasm shed; appears like sperm, but mature spermatid is still attached to Sertoli cell (see FIG. 8, j).

Sperm -- Male gamete.

I. Preparation of Testis Explant Cultures

According to the present invention, the screening test is performed using testis explant cultures, and in particular testis explant cultures from the male South African clawed frog *Xenopus laevis*. Testis explant cultures from other Xenopus species such as, *Xenopus mulleri* and *Xenopus borealis* can also be used for the screening test, but these species are not as easily obtained as are *Xenopus laevis*.

Hereinafter, the invention will be described with reference to *Xenopus laevis*, but it is to be understood that other species of Xenopus are included.

Animals

The male South African clawed frogs (*Xenopus laevis*) used in the present invention can be purchased commercially from the African Xenopus Facility, Cape Province, Republic of South Africa. Domestic sources include Xenopus I in Ann Arbor, Mich.; Nasco in Fort Atkinson, Wis.; and Charles D. Sullivan Co., Inc. in Nashville, Tenn. Also, several academic laboratories maintain breeding colonies of *Xenopus laevis* as well as *Xenopus Mulleri*, *Xenopus borealis* and other Xenopus species useful in the present invention.

The frogs are maintained according to conventional procedures. For example, the frogs can be kept in tap water in a room with a regulated temperature of 20° C.–24° C. and a 12 hr. light-dark cycle and fed a diet of frog brittle or Purina Trout chow. (manufactured by the Purina Company). The tap water should be dechlorinated and relatively free of organics. This can be achieved by conventional means, such as by filtration through charcoal filters.

Spermatogenesis is continuous in *Xenopus laevis*, and thus the frogs can be used to prepare testis explant cultures throughout the year.

The frogs can be sacrificed in any conventional manner, such as by decapitation, prior to dissection to remove the testes. Decapitation is preferred in order to avoid using anaesthesia.

Culture Media

The media used to culture the testis fragments are serum-free modifications of XSCM (Xenopus Spermatogenic Cell Medium), a medium previously shown to support the development of isolated spermatogenic cells from Xenopus (Risley. 1983 *Gam. Res.* 4:331–346). Two suitable media formulations are shown in the chart below.

| Serum-Free Media Formulations (mg/L) | | | |
|---|---|---|---|
| Meduim 1: | | | |
| NaCl | 3786 | Proline | 60 |
| KCl | 186 | Serine | 240 |
| $Na_2HPO_4 \cdot 12H_2O$ | 358 | Threonine | 70 |
| $CaCl_2 \cdot 2H_2O$ | 147 | Tryptophan | 20 |
| $MgCl_2 \cdot 6H_2O$ | 102 | Tyrosine | 40 |
| $MgSO_4 \cdot 7H_2O$ | 123 | Valine | 60 |
| $FeSO_4$ | 0.834 | Glucose | 1000 |
| HEPES (pH 7.4) | 3576 | Oxaloacetate | 152 |
| Alanine | 130 | Sodium Pyruvate | 110 |
| Arginine-HCl | 140 | Bovine Serum Albumin | 1000 |
| Aspartate-Mg | 450 | (CR,[1] fatty acid-free) | |
| Cysteine-HCl.$H_2O$ | 20 | Transferrin (human) | 10 |
| Cystine | 10 | BME Vitamin Mix[2] | (1X) |
| Glutamate-HCl | 1200 | Ascorbate | 50 |
| Glutamine | 292 | DL-a-Tocopherol | 0.2 |
| Glycine | 60 | Retinol | 0.029 |
| Histidine-HCl.$H_2O$ | 60 | Bovine Insulin (Zn) | 10 |
| Isoleucine | 50 | Dihydrotestosterone | 0.03 |
| Leucine | 80 | Testosterone | 0.03 |
| Lysine-HCl | 280 | $FSH^3$ (porcine) | 5 |
| Methionine | 50 | Antibiotic- | (1X) |
| Phenylalanine | 50 | Antimycotic Mix[4] | |
| Medium 2: | | | |
| As above, minus tocopherol, ascorbate and testosterone, supplemented with linoleic acid (5 μg/ml). | | | |

[1] = Collaborative Research, Waltham, Mass.
[2] BME = Basal Medium Eagles (NaCl 8.5 mg/L; Biotin 0.1 mg/L; D-Capantothenate 0.1 mg/L; Choline Chloride 0.1 mg/L; Folic Acid 0.1 mg/L; i-inositol 0.2 mg/L; Nicotinamide 0.1 mg/L; Pyridoxal HCL 0.1 mg/L; Riboflavin 0.01 mg/L; and Thiamine HCL 0.1 mg/L.)
[3] FHS = follicle-stimulating hormone
[4] 1X = 100 units/ml Penicillin; 100 mcg/ml streptomycin sulfate; 0.25 mcg/ml Fungizon4 (an antifungal agent manufactured by Gibco, Grand Island, N.Y.)

Inorganic components preferably are the purest grade available, i.e., reagent grade.

While not wanting to be bound by the validity of the reasons for the addition of specific supplements, the reasons for adding the supplements are as follows. BSA (bovine serum albumin), insulin, transferrin, dihydrotestosterone, and testosterone are added at concentrations which promote the development of isolated Xenopus spermatocytes in serum-free XSCM. FSH (follicle stimulating hormone) is added at a concentration that stimulates in vitro androgen production by Xenopus testes in short term cultures (Muller and Licht, 1980, *Gen. Comp. Endocrin.* 42:365–377). Vitamins A, E and C are included because they have been reported to have a beneficial effect on spermatocyte development in cultured mammalian testes (Steinberger et al., 1964. *Endocrinology* 74:788–792).

Media should be prepared fresh every two weeks with water purified by reverse osmosis and filtration through activated charcoal and deionizing columns and subsequent glass distillation. The media can be sterilized by filtration (0.2 μm filters) and stored at 4° C. During preparation, exposure of media to light should be minimized to avoid generation of photolytic byproducts. Retinol, tocopherol, and ascorbate should be omitted from stock solutions of media and added to media in subdued light just prior to each medium change. The osmolalities of the complete media (210–215 mOsm) all media stocks can be monitored with a freezing point depression osmometer.

Although extensive development of spermatogenic cells is supported by serum-free XSCM medium 1, this medium formulation is neither minimal nor optimal. This is clearly demonstrated by culturing testis fragments in serum-free medium 2 which lacks testosterone and vitamins E and C. Testis fragments are labelled in vitro with $^3$H-thymidine and cultured on filters for 35 days with medium 2. Autoradiography reveals that, similar to medium 1, medium 2 supports the development in 28 days of labelled spermatogonia into acrosomal vesicle spermatids (FIG. 5a). Fragments cultured 35 days contained labelled mature spermatids (FIG. 5b). This demonstrates that spermatogonia can develop to the mature spermatid stage in vitro, and tocopherol, ascorbate, and exogenous testosterone are not essential for the morphological development of most spermatogenic stages in Xenopus testes.

Further, cultured testes are not maintained in the same condition as uncultured testes. Some cells die while others survive and develop for 28–35 days.

More specifically, spermatogonial proliferation declines throughout the culture period resulting in poor replacement of developing spermatocytes and lobules are found in cultured testes which lack developing germ cells. Nevertheless sufficient numbers of the starting cell populations continue to develop into sperm through all stages of the spermatogenic cycle such that the inventive assays can be performed using these cultures.

Testis Explant Cultures

A. Filter/Grid Method: (Fell. H. B., 1953, *Sci. Progr.* 162:212 and Trowell. O. A., 1959. *Exp. Cell Res.* 16:118–147) Testes explant fragments can be prepared by cutting testes into 1–2 mm$^3$ fragments and culturing at an air-medium interphase in organ culture dishes. A suitable procedure is to place two to three fragments on a 5 mm$^2$ piece of cellulose nitrate filter, which is supported by a nylon screen in the center well of an organ culture dish, and then fill the center well with XSCM medium no. 1 (1–1.5 ml) until the medium contacts the support screen and is drawn by capillary action into the filter supporting the testis fragments. Distilled water is added to the outer well of the dish in order to maintain a humid atmosphere, and then each dish is wrapped in a flexible plastic wrap and placed in a humidified atmosphere of air maintained at about 20° to 24° C., preferably at about 22° C. Media is replaced with fresh media about every 2 to 3 days in order to avoid nutrient depletion and toxic by-product build-up.

In a scaled-up version of this procedure, 100–120 testes fragments can be cultured in a single 100 mm×100 mm×15 mm square petri dish with 40 ml medium. The fragments are cultured on a 30 μM mesh Nylon screen lying on a 1 mm mesh nylon screen supported by an appropriate object such as a bent plastic pipette lying on its side.

B. Tissue Culture Flask Method: Testis fragments can also be maintained in a partially submerged state in tissue culture flasks. Approximately 10 fragments/25 cm$^2$ flask surface area can be maintained with 3–4 ml of XSCM medium no. 1/25 cm$^2$ in tightly capped flasks. The fragment size is about 1 to 2 mm$^3$. The flasks are placed on a rocker platform in an incubator with the long axis of the flask oriented in the direction of rocking. Under these conditions, the testis fragments are alternately submerged and then exposed to air during the rocking cycle (4 oscillations/min). The temperature should be about 20° to 24° C., preferably about 22° C.

According to the above methods, testis fragments can be maintained in vitro for as long as 28 days. However, method A, the filter/grid method, is preferred because better maintenance of spermatogenesis can be achieved.

The gross histological organization of the testis fragments is maintained throughout the culture period. There are no necrotic foci in the fragments, but cells located at cut edges of the fragments are often degenerate. Further, the germinal epithelium in most seminiferous lobules remains intact and populated by spermatogenic cells in a typical cystic arrangement as shown in FIG. 1. However, occasional lobules with relatively few developing germ cells occur. Microscopic examination of the spermatogenic cells in 28 day cultures reveals the presence of cells at all stages of the spermatogenic cycle, including meiotic metaphase (FIG. 2a-d), but the relative numbers of secondary (type B) spermatogonia through leptotene spermatocytes decline between 14 and 28 days of culture.

Additionally, most spermatogenic stages progress and are not simply maintained in the cultured testis fragments. This is seen from autoradiography of sections from 14 to 28 day cultures of testis fragments incubated in vitro with $^3$H-thymidine on the first day of culture. Immediately following incubation with thymidine, testis fragments contain densely labelled spermatogonia (FIG. 3a). Due to the 7 day length of premeiotic S phase (Kalt, 1976, *J. Exp. Zool.* 195:393–408), cells at this stage incorporate relatively little thymidine during a 4 hr incubation and are difficult to detect following short autoradiographic exposures. After 14 days in culture, the testis fragments contain labelled spermatocytes, with late zygotene being the most advanced labelled stage (FIG. 3b). Fragments cultured for 28 days contain radiolabelled spermatids with prominent acrosomal vesicles (FIG. 3c). The density of silver grains over the spermatid nuclei is similar to that over nuclei of secondary spermatogonia on culture day 1. The development of late spermatogonial through mid-spermatid stages can be maintained for 28 days in Xenopus testis fragments cultured in serum-free XSCM medium 1.

The time required for the progression of labelled spermatogonia to spermatid stages in cultured Xenopus testis fragments at 22° C. is similar to the in vivo timing at 18° C. previously determined by Kalt, 1976, *J. Exp. Zool.* 195:393–408. A direct comparison of the timing of spermatogenesis in vitro and in vivo at 22° C. can be made by autoradiographic analysis of germ cell development in cultured testis fragments obtained from a frog injected with $^3$H-thymidine 15 days prior to dissection. The most advanced labelled spermatogenic cells present in these testes are spermatocytes at late zygotene or meiotic prophase (FIG. 4a), the same stage labelled by culturing testis fragments 14 days following in vitro incubation with thymidine. The grain density is considerably lower in the in vivo labelled cells. After 14 days of culture (29 days after in vivo exposure to thymidine), the most advanced labelled germ cells are at the acrosomal vesicle spermatid stage (FIG. 4b). The time required for the labelled spermatids to develop from spermatogonia is therefore similar whether spermatogonia are labelled in vitro on the first culture day or labelled in vivo 15 days prior to culture.

Testis fragments labelled in vivo and cultured for 28 days (43 days after exposure to thymidine) contain bundles of labelled mature spermatids embedded in Sertoli cells (FIG. 4c). The time required for the development of the mature spermatids agrees with the reported in vivo time, (Kalt, 1976, *J. Exp. Zool.* 195:393–408) Thus, all starting spermatogenic stages between type B spermatogonia and the terminal spermatid stages continue differentiating for extended periods at in vivo rates when Xenopus testis fragments are maintained in serum-free XSCM medium 1.

Efficiency of Maintenance of Spermatogenesis

A quantitative estimate of the efficiency of maintenance of spermatogenesis in vitro can be made by counting specific spermatogenic cells released from cultured testis fragments by collagenase. After 7–28 days in culture, fragments, e.g. 5–10, are removed from culture and dissociated with 0.2% collagenase (Risley and Eckhardt, 1979, *J. Exp. Zool.* 207:93–106). Differential cell counts can be performed with a hemacytometer using phase contrast optics (Risley and Eckhart, 1979, *J. Exp. Zool.* 207:93–106; Risley, 1983, *Gam. Res.* 4:331–346).

Assay for Development of Mature Sperm

Since sperm storage occurs in the testes of most amphibians, there are sperm present in the lumina of the seminiferous lobules at the beginning of each culture study. In order to differentiate between mature sperm that may develop in culture and sperm that are present from the start, autoradiography can be used as follows.

Testis explants (20–30 fragments, 1–2 mm³ in size) are incubated 4 hrs in XSCM medium 1 lacking unlabelled lysine and arginine, but supplemented with 5 μCi/ml each of L-4,5 ³H-lysine (79 Ci/mmol) and L-3,3,4,5 ³H-arginine (52 Ci/mmol). Most, i.e., about 90%, of the explants are then rinsed several times in fresh, complete XSCM medium 1 and cultured in tissue culture flasks. However, some of the explants are minced in complete XSCM media no. 1 immediately after labelling to release sperm from the lumina of the seminiferous lobules. Sperm can be collected from the media by centrifugation, for example at 2,500×g for 10 mins. The minced fragments can then be dissociated with collagenase to obtain the remaining testis cells, by known methods (Risley and Eckhardt, 1979, *J. Exp. Zool.* 207:93–106). For example, testes fragments are stirred or shaken for 1.5 to 2 hours in 0.2% collagenase prepared in 1X OR2 (82.5 mM NaCl; 2.5 mM KCl; 1.0 mM $CaCl_2$; 1.0 mM $MgCl_2$; 1.0 mM $Na_2HPO_4$; 5.0 mM HEPES; 3.8 mM NaOH). The cells released are then separated from undissociated tissue by filtration through Nylon mesh. The sperm collection procedure is then repeated on testis fragments cultured 10 days; however, the cultured fragments are first incubated for 15 hrs in XSCM medium 1 containing 50 Units/ml human chorionic gonadotropin (hCG) to stimulate the release of mature spermatids from Sertoli cells.

The conditions employed result in the incorporation of radiolabelled lysine and arginine primarily into the nuclei of spermatogonia and primary spermatocytes which synthesize histones and into mid-late spermatids which synthesize protamines (Risley, 1977, *Gam. Res.* 4:331–346). Most mature spermatids and sperm do not incorporate these amino acids into nuclear proteins. The appearance of sperm with radiolabelled nuclei in the lumina of the seminiferous lobules of cultured testis fragments is thus indicative of in vitro differentiation and release of sperm from Sertoli cells.

Labelled sperm obtained from minced or dissociated testis fragments can be identified by autoradiography of sperm nuclei spread on glass slides. Sperm or dissociated testis cells are incubated at room temperature in about 0.6% sodium citrate for about 20 min, fixed in methanol or methanol:acetic acid (3:1) according to conventional methods, and then spread on glass slides and air dried. The slides are coated with NTB2 autoradiographic emulsion (50%), manufactured by Kodak' Rochester. N.Y., exposed for 14 and 28 days at 4° C., developed, and subsequently stained with Giemsa (GURR, BDH Chemicals, England). The percent of labelled sperm nuclei in each preparation can then be determined, e.g., from counts of 150–200 sperm from each of 2 duplicate slides.

In a suitable 10 day culture, the percent of labelled sperm nuclei rises from 6% on day 1 to 40–55% on day 10.

Sperm Motility Assays and Artificial Fertilizations

In order to determine if the sperm produced in vitro are functional, the motility and fecundity of sperm obtained from cultured testis fragments can be examined as follows.

Testis fragments are cultured in flasks with XSCM medium 1 for 35 days. On days 9, 20 and 34, hCG (50 U/ml) is added to the media. After incubation in hCG for 15 hrs, fragments are either returned to fresh medium 1 lacking hCG for further culture or are minced in cold (4° C), hypertonic 1.5X OR2 (123.75 mM NaCl; 3.75 mM Kcl: 1.5 mM $CaCl_2$ 1.5 mM $MgCl_2$, 1.5 mM $Na_2HPO_4$; 7.5 mM HEPES. 5.7 mM NaOH) (Wallace et al., 1973, *J. Exp. Zool.* 184:321-334) or a 3X solution of Fl(123.75 mM NaCl: 3.75 mM KCl; 0.75 mM $CaCl_2$; 0.1875 mM $MgCl_2$; 1.5 mM $Na_2HPO_4$; 7.5 mM HEPES: 5.7 mM NaOH) to release sperm and preserve their motility and fecundity (Hollinger and Corton, 1980, *Gam. Res.* 3 45–57). Both solutions are modified to contain about 5.5 mM glucose and about 1 mM sodium pyruvate. Sperm released into the buffered salt solutions can be stored at 4° C. until used. Sperm (controls) are also obtained by mincing testes immediately after dissection or after a 15 hr incubation of testis fragments in medium 1 containing hCG.

For motility assays, aliquots of each sperm suspension are diluted with 2 volumes of distilled water to activate motility, and the percent of sperm exhibiting distinct swimming motions is determined using wet mounts and phase contrast optics (Hollinger and Corten, 1980, *Gam. Res.* 3:45-57). All counts should be conducted within 5 minutes of dilution of the sperm suspension. Total sperm numbers can be counted using a hemacytometer.

Artificial fertilizations can be conducted essentially as described by Hollinger and Corten, 1980. *Gam. Res.* 3:45–57. Eggs are collected from female *Xenopus laevis* injected with 50–100 units of hCG on the prior day and 1000 units of hCG in the morning of the day of collection. At the first indication of egg laying, the females are transferred to 1.5X OR2 or 3X F1, and eggs are collected by pipette as they are shed. The eggs are placed in small beakers or petri dishes in groups of about 30, and are mixed with sperm within about 15-30 minutes. Just prior to mixing with sperm, the hypertonic salt solution is removed from the eggs. A specific number of sperm in a small volume (20-200 μl) of 3X F1 is then added to the vessel in a region separate from the eggs. A solution of 1X F1 (3 ml) is then added to the vessel and the sperm and eggs are mixed rapidly. The F1 solution is replaced within 4-12 hrs by solution DB (110 mM NaCl: 1.3 mM KCl: 0.44 mM $CaCl_2$, pH 7.2). (Wolf and Hedrick, 1971, *Develop. Biol.* 25:348-359) and unfertilized eggs are removed. All subsequent development is allowed to occur in solution DB. Indexes of fecundity and normal development can be obtained from counts of normal cleaving embryos and counts of cleavage stage embryos that develop to tadpole stages 39-40 i.e., swimming tadpoles (Nieuwkoop and Faber, 1956, Normal table of *Xenopus laevis* (Daudin); Amsterdam: North-Holland Publ.).

Sperm from cultured testes are considered functional if at several different concentrations they show equivalent ability to sperm taken directly from frogs, i.e., the percent of eggs fertilized is comparable and the percent fertilized eggs that develop normally is comparable.

II. Screening Test for Mutagenicity and Genotoxicity

The screening test for mutagenicity and genotoxicity of various test agents according to the present invention is conducted using *Xenopus laevis* testis explants cultured as described above.

In order to conduct the screening test, the *Xenopus laevis* testis explants, are cultured in the presence of one or more test agents. Mixtures of test agents can be used, for example, to determine possible synergistic effects. Solvent controls are run in parallel in order to determine nonspecific effects due to the solvent used to dissolve the test agent(s). A positive control (e.g. $10^{-5}$ M Adriamycin) can also run concurrently to ensure that the test is performing properly. After an appropriate exposure period, the test agent(s) is removed and culture is continued such that spermatogonia in the *Xenopus laevis* explants undergo spermatogenesis. After appropriate times, sperm and/or one or more types of spermatogenic cells is/are isolated and the mutagenic and/or genotoxic affect of the test agent(s) is determined by various assays. Importantly, this screening test can also be used to concurrently test multiple genetic endpoints.

Exposure Of Testes To Test Agent

Minced testis fragments are exposed to the test agent as soon as the organ cultures are set up (1-2 hour after dissection).

Testis fragments are incubated with the test agent in serum-free XSCM medium 1 lacking BSA, vitamin E and Vitamin C.

If necessary, the test agent is first dissolved in sterile water or other appropriate solvent. Desirably, at least 2 independent replicates are used for each control and test agent concentration.

For initial studies, the amount of test agent to be added usually extends over a concentration range of $10^{-7}M-10^{-4}M$ in steps of 10X. Subsequent studies use doses within the effective dose range determined by the initial studies.

Usually a range of concentrations of test agent will be used.

Parallel controls are run which receive water or other solvent without test agent. Of course, if test agent was added without first dissolving in solvent, no solvent is added to the control.

After adding the test agent, cultures are incubated for 4 (but preferably 12) to 72 hours. There is no known upper limit. The lower limit is dependent upon the time required for penetration of the testis fragment by the test agent. Incubation conditions are the same as those described above for cultures without test agent.

To remove test agent, fragments are rinsed extensively with 1X OR2, described above (Wallace et al 1972, *J. Exp. Zool.* 184:321-334) and fresh, complete serum-free XSCM is added to the fragments.

The fragments are then cultured for 2-30 days in complete XSCM medium 1 described above in 75 $cm^2$ tissue culture flasks or preferably in scaled-up versions of the filter/grid method in which 100-120 testis fragments are cultured on nylon screens in 100 mm×100 mm×15 mm petri dishes with 40-50 ml medium.

Determination of Mutagenicity and/or Genotoxicity of Test Agent(s)

In order to determine the mutagenicity and/or genotoxicity of the test agent, samples of sperm and/or one or more types of spermatogenic cells are removed from the culture at appropriate intervals after exposure to test agent and then subjected to the desired assay(s).

The times at which samples are removed depends upon the particular assay(s) that is to be conducted and can readily be determined by the skilled artisan.

Samples are removed by taking fragments from each treatment group from the culture vessel.

Sperm and/or different cell types can be separated from the samples as follows.

Testes are dissociated with collagenase (Risley, M. S. & Eckhardt, R. A., 1979, *J. Exp. Zool.* 207:93-106) to release intact spermatogenic cells. Sperm can be obtained by simply mincing the testes. Collagenase dissociated spermatogenic cells can be separated using density-gradient centrifugation and unit gravity sedimentation to isolate cells in specific stages of spermatogenesis (Risley & Eckhardt, 1979. *J. Exp. Zool.* 207:93-106).

For example, dissociated spermatogenic cells can be centrifuged in either 10-12% metrizamide (Risley and Eckhardt), 1979. *J. Exp. Zool.* 207:93-106) or 28% Percoll (a silica gel coated with polyvinyl pyrollidone manufactured by Pharmacia, Uppsala, Sweden) to pellet sperm, late spermatids, residual bodies, and most somatic cells, but float spermatogonial through mid-spermatid stages (including meiotic metaphases and round spermatids). Unit gravity sedimentation can be used to separate the spermatogonia, spermatocytes and early-mid spermatids if desired.

Possible assays that can be used to determine mutagenicity and/or genotoxicity of the test agent are numerous and include assays well known to those skilled in the art as well as assays proposed for the first time by the present inventors.

Examples of assays to those skilled in the art include dominant lethal assays (Hemsworth, et al. 1978, *Mutat. Res.* 51:45-53; Jones et al, 1974, *J. Reprod. Fertil.* 38:347-357); cytogenetic analysis of primary and secondary spermatocyte chromosomes (I.-D. Adler, 1984. Cytogenetic tests in mammals. In "Mutagenicty Testing, A Practical Approach" (S. Venitt and J. M. Parry. eds.) IRL Press, Washington D.C., pp. 275-306); alkaline elution of DNA (Sega et al, 1986, *Mutat. Res.* 159:55–63; Sega et al, 1982, *Environ. Mutagen.* 4:347–347; Skare and Schrotel, 1984, *Mutat. Res.* 130:283–294; Skare and Schrotel, 1984, *Mutat. Res.* 130:294–303); and micronucleus assays (Lähdetie and Parvinen, 1981; *Mutat. Res.* 81:103–115).

An example of an assay proposed for the first time by the present inventors is a recessive lethal assay.

By way of example, not intended to be limiting, some of the possible assays that can be performed on samples isolated from the in vitro Xenopus cultures are described below.

In vitro Dominant Lethal Assay

In vitro dominant lethal assays detect mutations or chromosome abberations causing death of an embryo. Eggs are fertilized in vitro with the sperm of interest and then the embryos thus produced are examined with a dissection microscope to determine the frequency of abnormalities and developmental arrests. (See, for example, Hemsworth, et. al. 1978, *Mutat. Res.* 51:45–53 and Jones et al, 1974, *J. Reprod. Fertil.* 38:347–357)

In the present system, sperm from cultured control and test agent exposed testes can be collected as described above for the sperm motility assays and artificial fertilizations and used to fertilize eggs also as described above. The embryos produced can be examined by the conventional techniques.

Cytogenetics Analysis of Primary and Secondary Spermatocyte Chromosomes

Cytogenetics are used to detect alterations in either chromosome number or chromosome structural integrity.

Chromosomes from spermatocytes in meiotic metaphases I and II, i.e., primary and secondary spermatocytes, can be examined by cytogenetic techniques by arresting the spermatocytes in meiotic metaphases I and II after incubation with colchicine or colcemid (I.-D. Adler. 1984. Cytogenetic tests in mammals. In "Mutagenicity Testing, A Practical Approach" (S. Venitt and J. M. Parry. eds.) IRL Press, Washington D.C., pp. 275–306).

In the present system. spermatocytes can be arrested in meiotic metaphases I and II by incubating cultured testes with colchicine (about 1 µg/ml) or colcemid (about 1–2 µg/ml) for about 16 to 18 hours. The testes can then be dissociated with collagenase and the spermatocytes isolated, as described above, for cytogenetic analysis of the chromosomes.

Sufficient numbers of spermatocytes in meiotic metaphases I and II for cytogenetic analysis of the chromosomes can be obtained from about 5 to 10 testes fragments.

Alkaline Elution of DNA

Alkaline elution of DNA detects unrepaired DNA damage.

The assay can be applied to nuclear DNA from any spermatogenic cell type or sperm.

The alkaline elution technique can detect changes in the average size of DNA strands by measuring the rate at which alkaline buffers elute DNA from polycarbonate or polyvinyl filters. The filters trap DNA double stranded molecules with an efficiency that is dependent upon DNA length. Alkaline buffers are then used to elute DNA single strands from the filters at a rate that is inversely proportional to the length of single stranded DNA and directly proportional to the number of single strand breaks present in the DNA. In addition to detecting DNA single strand breaks, the alkaline elution assay may also be employed to estimate the relative content of interstrand DNA cross-links and DNA-protein cross-links. (See, for example. Sega et al, 1986, *Mutat. Res.* 159:55–63; Sega et al, 1982, *Environ. Mutagen.* 4:347–347; Skare and Schrotel, 1984, *Mutat. Res,* 130:283–294; Skare and Schrotel, 1984, *Mutat. Res,* 130:295–303

Micronucleus Assay

The micronucleus assay detects chromosome breakage and nondisjunction.

Micronuclei occur in round spermatids as a consequence of chromosome damage in pre-spermatid stages, i.e. spermatocytes and spermatogonia, etc. Micronuclei can be detected by fluorescence microscopy of spermatids stained with the DNA specific fluorochrome, Hoechst 33258. (See, for example, Lähdetie and Parvinen, 1981, *Mutat. Res.* 81:103–115 Lähdetie, J. 1983, *Mutat. Res.* 119:79–82 and 120:257–260).

In the present system, by periodically collecting spermatids from testes cultured for 3 to 30 days and scoring micronuclei, the chromosome damage leading to the micronuclei formation can be traced to one or more specific pre-spermatid stages.

In vitro Recessive Lethal Assay

In vitro recessive lethal assays proposed for the first time by the present inventors detect mutations in paternal genes essential for embryonic development. Sperm are used to fertilize eggs that have had the maternal genome destroyed prior to fertilization, for example, by irradiation with U.V. light or X-rays. Following fertilization, the eggs are incubated at low temperature (e.g. 4° C.) for 10 min. to block cytokinesis and then returned to normal temperature (e.g. 20° C.). This procedure permits the paternal genome to diploidize. The embryos are then analyzed during development to quantitate paternal recessive lethals - a potentially very sensitive assay since many genes are important for normal development. The frequency of lethality equals the percent of embryos that die or arrest development by stages 39–40 (swimming tadpole).

As mentioned above, an important aspect of the present screening test is that it can be a multi-endpoint test. That is, a screening test can test several different genetic parameters, such as heritable mutations (dominant or recessive lethal), chromosome breaks, chromosome number, DNA integrity (alkaline elution assay), etc.

Testing of more than one genetic parameter in one screening test is accomplished by simultaneously isolating sperm and/or one or more types of spermatogenic cells as described above and then performing one or more assays on each of the types of cells isolated.

According to this embodiment of the present invention, any number of combinations of assays can be employed.

For example, routine cytogenetic assays of cultured spermatocyte chromosomes from metaphases I and II can be employed to characterize aberrations detected in a micronucleus screening assay. Indeed, concurrent micronucleus and cytogenetic assays can be conducted since primary and secondary spermatocytes can be isolated together with round spermatids using the cell separation methods described above. A test consisting of micronucleus assays and subsequent metaphase II cytogenetics assays of cells from selected treatment groups can be used to analyze meiotic aneuploidy.

Additionally, since fertile sperm are produced in cultured testes according to the present invention, developing sperm can be periodicially collected from cultured, mutagen treated testes for biochemical analysis (i.e. alkaline elution assay) or for the analysis of heritable mutations in embryos produced by artificial fertilization of Xenopus eggs. This approach permits in vitro evaluations of the induction of both chromosome aberrations and heritable mutations in most spermatogenic stages.

In fact, concurrent screening tests can be conducted for heritable mutations, meiotic chromosome aberrations, spermatid micronucleus, sperm DNA single strand breaks, and sperm chromosome aberrations, etc.

Further, concurrent assays permit the evaluation of the survival of different types of aberrations from one spermatogenic stage to the next by, for example, analysis of the frequency of aneuploidy at metaphase II and in sperm at various times after exposure of testes to the test agent. If metaphase II aneuploidy is measured at, e.g. 2%, then, assuming a lack of selection against aneuploid cells, sperm which develop (~18 days) from the metaphase II cells should exhibit 2% aneuploidy. Significant reductions in the sperm aneuploid values relative to metaphase II aneuploidy suggests post-meiotic selection. A similar approach can be used to detect selection against specific chromosome breaks. Comparisons of spermatid to sperm DNA alkaline elution assays will indicate whether DNA breaks or cross-links induced in spermatids are resolved or selected against before the spermatids become sperm.

EXAMPLES

The invention will now be illustrated by reference to specific examples. However, the invention should not be construed as being limited thereto.

Unless otherwise specified, all ratios, percents, etc., are by weight.

EXAMPLE 1

In Vitro Spermatid Micronucleus Assay

Animals and Test Agents

Male South African clawed frogs (*Xenopus laevis*) were obtained from domestic importers (Xenopus I. Ann Arbor, Mich.; Charles D. Sullivan Co., Inc., Nashville, Tenn.) and maintained in tap water in a room with a regulated temperature of 20° C. to 24° C. and a 12 hr. light-dark cycle. The frogs were sacrificed by decapitation prior to dissection.

Three well characterized clastogens were used in this Example: a polycyclic aromatic hydrocarbon (9,10-dimethyl-1,2-benzanthracene, DMBA; CAS # 65763-31-7). a nitrogen mustard (cyclophosphamide, CP: CAS # 50-18-0). and an anthracycline antibiotic (adriamycin, AD; CAS # 25316-40-9). Each test agent was purchased from Sigma Chem. Co. (St. Louis, Mo.).

Testis Explant Cultures

Testes were dissected aseptically from male frogs and cut into 1–2 mm$^3$ fragments (about 20 fragments/testis) in serum-free, hormone supplemented XSCM (Xenopus Spermatogenic Cell Medium) described above (Medium 1) lacking bovine serum albumin and vitamins E and C. The fragments were then placed into 75 cm$^2$ flasks (35 fragments/flask) with 10 ml of the same medium. Ten flasks were employed in a study comprised of two independent replicates of a concurrent control group and each of four different concentrations of a test agent. Each flask contained a sufficient number of testis fragments to conduct spermatid micronucleus assays at seven different time points (5–6 fragments per assay) following exposure to a test agent.

Test agents were added to each flask from concentrated stocks prepared in sterile water or DMSO (dimethylsulfoxide) immediately prior to use. Controls received either water or DMSO alone; the final concentration of DMSO was 0.1% in all cases. The flasks were rocked (4 oscillations/min) in an incubator at 22° C. for the duration of the test agent exposure period.

After incubation with the test agent, fragments were rinsed extensively with 1X OR2 (82.5 mM NaCl; 2.5 mM KCl; 1.0 mM CaCl$_2$; 1.0 mM MgCl$_2$; 1.0 mM Na$_2$HPO$_4$; 5.0 mM HEPES; 3.8 mM NaOH) (Wallace et al., 1972, *J. Exp. Zool.* 184:321–334) and fresh, complete serum-free XSCM was added to each flask. The fragments were then cultured in flasks for 2–30 days in complete XSCM as follows.

Fragments were placed in tissue culture flasks in an amount of about 10 fragments/25 cm$^2$ of flask surface area and medium was added in an amount of about 3–4 ml/25 cm$^2$ of flask surface area. The flasks were tightly capped and placed on a rocker platform in a 22° C. incubator with the long axis of the flask oriented in the direction of rocking. The rocking cycle was about 4 oscillations/min. Under these conditions, the testis fragments were alternately submerged and then exposed to air during the rocking cycle.

Spermatid Micronucleus Assays

Chromosome aberrations induced in developing spermatocytes were detected as micronuclei in round spermatids (cf Lähdetie and Parvinen, 1981, *Mutat. Res.* 81:103–115). To analyze all spermatocyte stages, including premeiotic S phase spermatocytes, spermatids were isolated from cultured testis fragments on days 3, 6, 9, 16, 22 (or 23) and 30 of total culture time, including the period of incubation with each mutagen. These time intervals correspond to those required for in vivo (Kalt, 1976, *J. Exp. Zool.* 195:393–408) or in vitro development of round spermatids from diplotene through metaphase II (3 days), late pachytene to diplotene (6 days), mid-pachytene (9 days), zygotene to early pachytene (16 days), leptotene to early zygotene (22 and 23 days), and premeiotic S plus late type B spermatogonia (30 days). Due to the 7 day length of premeiotic S (Kalt. M. R., 1976, *J. Exp. Zool.* 195:393–408) and the 5–6 day length of the round spermatid stage (Risley. M. S., 1983, *Gam. Res.* 7:331–346) the majority of round spermatids in 30 day testis cultures developed from premeiotic S phase.

At the appropriate time, 5–6 fragments were removed from each flask and enzymatically dissociated by continuous mixing (Roto-Torque Mixer, setting 5) in 7 ml of 0.2% collagenase (Type I. Sigma Chem. Co., St. Louis. Mo.) prepared in 1X OR2 containing 1 mM each of pyruvate and oxaloacetate, 5.5 mM glucose, and 0.1% polyvinylpyrrolidone and bovine serum albumin. After dissociation. DNase I was added (to 5 μg/ml) for 10 mins. to digest released DNA, followed by addition of fetal calf serum to 5%. The suspension was then filtered through nylon screens to remove undissociated tissue and cell aggregates.

Dissociated cells were pelleted by centrifugation at 850×g (IEC HNS II centrifuge, 958 rotor, ambient temperature) and separated by centrifugation in Percoll (a silica gel coated with polyvinyl pyrrolidone manufactured by Pharmacia, Uppsala, Sweden) step-gradients. Cells in 2.5 ml 30% Percoll-OR2 (1X) were added to 15 ml conical centrifuge tubes, overlaid with 1 ml 10% Percoll-OR2 (1X). and centrifuged at 1000×g. The supernatants, enriched for spermatogonial through round spermatid stages, were collected, diluted with 3 vols of OR2, and pelleted as described above. The cells were resuspended in 0.1-0.2 ml 1X OR2 and fixed by addition of 2 ml 2% glutaraldehyde, 0.06 M cacodylate-HCL (pH 7.2) for 2 hr at 4° C. After fixation, the cells were rinsed with 0.1 M cacodylate-HCl (pH 7.2) and stored at 0-5° C. in 1 ml of this buffer.

Micronucleus assays were modified from those described by Lähdetie and Parvinen, 1981, Mutat. Res. 81:103-115. Fixed spermatogenic cells (1-3×10$^6$) were pelleted and resuspended in 0.2-0.3 ml of 0.1 M cacodylate-HCL containing 5 ug/ml of the DNA specific fluorochrome Hoechst 33258 (Calbiochem, La Jolla, Calif.) and 2% 2-mercaptoethanol. The suspension was then added to the wells (0.1 ml/well) of a flat-bottomed 96 well tissue culture plate. After the cells sedimented onto the surface of each well (30 mins), the cells were examined with a Nikon Diaphot inverted microscope equipped with epiflourescence and optics for simultaneous fluorescence and phase contrast or Hoffman Modulation microscopy.

Round spermatids (500-1200/replicate) with prominent acrosomal vesicles (see FIG. 6) were examined for the presence of fluorescent micronuclei. This spermatid stage in Xenopus has been characterized morphologically in previous reports (Reed and Stanley, 1972, Ultrastruct. Res. 41:277-295). Spermatid symplasts were not analyzed; only single spermatids with typical morphologies were included. Only Hoechst positive bodies clearly separated from the nucleus were counted as micronuclei. Spermatids with more than one micronucleus were rare and were therefore not treated as a separate category. The mean percent of round spermatids with micronuclei was obtained from two independent replicates. The number of spermatids with and without micronuclei in both replicates (1000-2400 spermatids) of a treatment group were pooled and compared statistically to similarly pooled data from concurrent control replicates by exact calculation of P for 2×2 contingency tables using a single-tailed Fisher's Exact Test (c.f. Ehrenberg, L., 1984, Aspects of statistical inference in testing for genetic toxicity, in: B. J. Kilbey et al. (Eds.), Handbook of Mutagenicity Test Procedures, Elsevier, Amsterdam, pp. 775-822)

In Vitro Assay Using Cyclophosphamide (CP)

Cyclophosphamide is a nitrogen mustard derivative that requires metabolic activation for mutagenesis (Mohn, G. R., and J. Ellenberger, 1976, Mutation Res. 32:331-360). Incubation of testis explants (without exogenous activation systems) for 24 hr with $10^{-7}$ M (28 µg/L) to $10^{-4}$ M (28 mg/L) CP did not result in a significant induction of spermatid micronuclei relative to concurrent controls until 29 days after exposure or 30 culture days. At 29 days, there was a dose-dependent increase in spermatid micronuclei, with the lowest effective dose being $10^{-6}$ M (0.28 mg/L). The results are shown in Table 1 below and graphically illustrated in FIG. 7.

TABLE 1

Percent Round Spermatids With Micronuclei In Cultured Testes Incubated 24 Hrs. With CP[a]

| CP (moles/L) | Post-CP Culture Period | | | | | |
|---|---|---|---|---|---|---|
| | Day 2 | Day 5 | Day 8 | Day 15 | Day 21 | Day 29 |
| 0 | .20 +/− .001 | .18 +/− .02 | .10 +/− .13 | .30 +/− .15 | .25 +/− .07 | .38 +/− .02 |
| $10^{-7}$ | .15 +/− .03 | .15 +/− .04 | .20 +/− .01 | .29 +/− 1.15 | .25 +/− .08 | .70 +/− .14 |
| $10^{-6}$ | .37 +/− .28 | .37 +/− .29 | .15 +/− .06 | .49 +/− .13 | .35 +/− .07 | .99 +/− .01* |
| $10^{-5}$ | .20 +/− .01 | .19 +/− .01 | .29 +/− .14 | .38 +/− .26 | .41 +/− .16 | 1.90 +/− .43** |
| $10^{-4}$ | .30 +/− .14 | .29 +/− .14 | .29 +/− .13 | ND | .25 +/− .07 | 2.70 +/− .13*** |

[a]Data are presented as means (+/− s.d.) of two independent replicates.
ND, not determined.
*p < .05;
**P < .01;
***p < .001 (Fisher's Exact Test).

The results demonstrate that in vitro exposure of testis explants to CP induces aberrations in cells that require 24 to 30 days to develop into round spermatids.

The results also demonstrate that the in vitro assay of the present invention is capable of detecting agents that require metabolic activation.

In Xenopus, the majority of round spermatids present at 30 days of culture develop from the premeiotic S phase, but some also develop from late type B spermatogonia. The restriction of CP clastogenesis to premeiotic stages in cultured testes is consistent with the results from an in vivo rat spermatid micronucleus assay (Lähdetie, 1983, Mutat. Res. 120:257-260) and an in vivo mouse synaptonemal complex assay for CP induced chromosome aberrations (Allen et al., 1987, Mutat. Res. 190:19-24).

The results presented in Table 1 are inconsistent with a report by Pacchierotti et al., 1983, Mutat. Res. 119:177-183, which described CP induction of chromosome aberrations throughout meiotic prophase in the male mouse. The micronucleus assays were therefore repeated using a 72 hr CP incubation period to increase the opportunity for in vitro CP clastogenesis in non-S phase spermatocytes. Micronuclei were scored in spermatids from 9 day cultures (3 day CP incubation and 6 day culture) to evaluate clastogenesis in pachytene through diplotene spermatocytes.

The results are shown in Table 2 below.

TABLE 2

Percent Round Spermatids With Micronuclei In Testes Cultured 6 Days Aftr A 72 Hr. Incubation With CP

| CP moles/L | Micronucleus % |
|---|---|
| 0 | .12 +/− .06 |
| $10^{-7}$ | .15 +/− .06 |
| $10^{-6}$ | .14 +/− .06 |
| $10^{-5}$ | .19 +/− .01 |
| $10^{-4}$ | .27 +/− .11 |

[a]Data are means (+/− s.d.) of two independent replicates.

Table 2 shows that a 72 hr incubation with CP did not result in significant increases in micronuclei in spermatids which develop from pachytene through diplotene stages of meiotic prophase.

It should be noted that there was usually no significant change in the spermatid micronucleus frequency in control cultures throughout the 30 day culture period, even when compared to the in vivo spermatid micronucleus frequency in Xenopus (0.21%; 16 micronuclei/7675 spermatids from 4 separate dissociations, 20 testes per dissociation). Occasionally, however, the control micronucleus frequencies in 30 day cultures showed an unexplained significant increase. Frequently, small Hoechst positive particles were found associated with the cells isolated from these cultures, suggesting possible mycoplasmal contamination. On such occasions, data obtained from all cultures on that day were rejected.

In Vito Assay Using 9,10-Dimethyl-1,2-benzanthracene (DMBA)

DMBA is a polycyclic aromatic hydrocarbon which requires metabolic activation to form the mutagenic dihydrodiol and epoxide derivatives (Marquart et al., 1978, *Biochem. Biophys. Res. Comm.* 85:357–362). A 24 hr. exposure of testis explants to DMBA resulted in a dose-dependent increase in the spermatid micronucleus frequency only after 29 additional days of culture, as expected for a clastogen with S-dependent activity in premeiotic S spermatocytes. The results are shown in Table 3 below and graphically illustrated in FIG. 7. The solvent (0.1% DMSO) had no significant effect on the micronucleus frequency as judged from a comparison of the concurrent controls. Clastogenesis by DMBA was directly proportional to exposure time since a 72 hr. incubation of testis explants in $10^{-5}$M (2.6 mg/L) DMBA increased the spermatid micronucleus frequency on culture day 30 by 3 fold relative to that resulting from a 24 hr. incubation. The results are shown in Table 4 below.

TABLE 4

Percent Round Spermatids With Micronuclei In Cultured Testes Incubated With DMBA For 24 and 72 Hrs.[a]

| DMBA (moles/L) | Incubation Period | |
|---|---|---|
| | 24 hr. | 72 hr. |
| 0 | .34 +/− .09 | .44 +/− .07 |
| $10^{-5}$ | .86 +/− .10* | 2.52 +/− .44*** |

[a]Testes were incubated in media containing DMBA or 0.1% DMSO for 24 and 72 hr. and were cultured subsequently for 29 and 27 days, respectively.
*$P < .05$
***$P < .001$ The results from the DMBA study agree with the stage specific effects of DMBA noted in an in vivo rat spermatid micronucleus assay (Lähdetie, 1983, *Mutat. Res.* 120:257–260) and confirm that the in vitro assay of the present invention is capable of detecting agents that require metabolic activation.

In Vitro Assay Using Adriamycin (AD)

In contrast to the S-dependent effects of DMBA and CP, exposure of testis explants to AD for 4 hrs. resulted in dose-dependent increases in spermatid micronuclei at each time point examined as shown in Table 5 below, indicating that AD induced chromosome aberrations in all stages of spermatocyte development. The spermatocyte stages most sensitive to AD clastogenesis appeared to be leptotene (day 23) and premeiotic S or type B spermatogonia (day 30). These results are consistent with previous in vivo assays for AD clastogenesis in rat spermatocytes (Au and Hsu, 1980, *J. Mol. Biol.* 12:581–599; Lähdetie, 1983, *Mutat. Res.* 119:79–82).

TABLE 5

Percent Round Spermatids With Micronuclei In Cultured Testes Incubated 4 Hrs. With AD[a]

| AD (moles/L) | Post-AD Culture Period | | | | | |
|---|---|---|---|---|---|---|
| | Day 3 | Day 6 | Day 9 | Day 16 | Day 23 | Day 30 |
| 0 | .16 +/− .03 | .23 +/− .02 | .43 +/− .08 | .19 +/− .12 | .66 +/− .15 | .53 +/− .22 |
| $10^{-6}$ | .20 +/− .28 | .24 +/− .09 | .33 +/− .16 | .48 +/− .22 | .85 +/− .22 | 1.65 +/− .07** |
| $5 \times 10^{-6}$ | .18 +/− .01 | .53 +/− .07 | .86 +/− .06 | 1.10 +/− 0** | 2.45 +/− .07*** | 3.30 +/− .57*** |
| $10^{-5}$ | .27 +/− .12 | .65 +/− .28 | 1.95 +/− .49** | ND | ND | ND |
| $10^{-4}$ | .91 +/− .04** | 1.25 +/− .21** | 2.40 +/− .28*** | ND | ND | ND |

[a]Cultures were maintained in serum-free XSCM medium 1 supplemented with palmitate (62 μM), linoleate (25 μM), selenous acid (2 × $10^{-8}$ M), and trace element mix (MnSO$_4$.H$_2$O .0017 μg/L, Na$_2$SiO$_3$.9H$_2$O 1.42 μg/L, (NH$_4$)$_6$MO$_7$O$_{24}$.4H$_2$ .0124 μg/L, NH$_4$SO$_3$ .00585 g/L, NiCl$_2$.6H$_2$O .00119 μg/L, SnCl$_2$.2H$_2$O.00113 μg/L). Data are means (+/− s.d.) of two independent replicates.
ND, not determined.
*$p < .05$;
**$p < .01$;
***$p < .001$.

The results presented in Table 5 were derived from AD assays of testis explants cultured in serum-free XSCM medium 1 supplemented with fatty acids, selenous acid and several trace elements (see legend to Table 5).

TABLE 3

Percent Round Spermatids With Micronuclei In Cultured Testes Incubated 24 Hrs. With DMBA[a]

| DMBA (moles/L) | Post-DMBA Culture Period | | | | | |
|---|---|---|---|---|---|---|
| | Day 2 | Day 5 | Day 8 | Day 15 | Day 22 | Day 29 |
| 0 | .16 +/− .04 | .15 +/− .03 | .39 +/− .28 | .29 +/− .13 | .29 +/− .13 | .34 +/− .07 |
| $10^{-7}$ | .29 +/− .14 | .16 +/− .06 | .21 +/− .02 | .28 +/− .13 | .19 +/− .02 | .36 +/− .05 |
| $10^{-6}$ | .28 +/− .13 | .15 +/− .06 | .16 +/− .06 | .39 +/− .01 | .30 +/− .14 | .68 +/− .01* |
| $10^{-5}$ | .19 +/− .01 | .16 +/− .06 | .39 +/− .28 | .20 +/− .001 | .48 +/− .13 | .83 +/− .06** |
| $10^{-4}$ | .16 +/− .04 | .15 +/− .06 | .17 +/− .05 | .48 +/− .12 | .28 +/− .12 | 1.07 +/− .14*** |

[a]Testes were incubated 24 hrs in media containing 9,10-dimethyl-1,2-benzanthracene and 0.1% DMSO or 0.1% DMSO (control). Data are presented as means (+/− s.d.) of two independent replicates.
*$p < .05$;
**$p < .01$;
***$p < .001$.

Since the concurrent controls showed an elevated level of spermatid micronuclei on days 23 and 30, there was a possibility that the medium supplements may have been responsible and may have augmented AD effects. The AD assays were therefore repeated for the leptotene (day 22) and premeiotic S (day 30) stages using unmodified serum-free medium 1, the same medium used in the DMBA and CP assays. In addition, the low AD test concentration was reduced to $10^{-7}$ M (58 µg/L).

The data are shown in Table 6 and graphically illustrated in FIG. 7.

TABLE 6

Percent Round Spermatids With Micronuclei In Testes Cultured 22 and 30 Days After A 4 Hr. Incubation With Ad[a]

| AD (moles/L) | Post-Ad Culture Period | |
|---|---|---|
| | Day 22 | Day 30 |
| 0 | .25 +/− .07 | .38 +/− .02 |
| $10^{-7}$ | .30 +/− .14 | 1.04 +/− .08** |
| $10^{-6}$ | .88 +/− .12* | 1.83 +/− .11*** |
| $5 \times 10^{-6}$ | 1.43 +/− .04*** | 3.09 +/− .40*** |

[a]Data are means (+/−s.d) of two independent replicates.
*P < .05
**P < .01
***P < .001

The data in Table 6 show that the micronucleus counts in the concurrent controls did not increase significantly on day 22 or day 30 when unmodified XSCM was used in the AD assays. Consistent with the results in Table 5, a 4 hr. exposure of testes to AD resulted in a dose-dependent increase in spermatid micronuclei on both days 22 and 30 Table 6). As a result of the reduced levels of micronuclei in the concurrent controls the assay was sensitive to clastogenesis by $10^{-6}$ M (0.58 mg/L) AD on day 22 and $10^{-7}$ M (58 µg/L) AD on day 30. Further, a significant increase (1.7 fold) in assay sensitivity could be achieved by increasing the exposure to AD from 4 hrs. to 12 hrs. to permit greater penetration of the testis fragments.

Comparison of Results of CP, DMBA, & AD In Vitro Assays

FIG. 7 shows a graphic comparison of the day 30 micronucleus counts obtained from the CP (Table 1). DMBA (Table 3) and AD (Table 6) studies as a function of the product of mutagen dose and exposure time. This comparison clearly shows that the relative in vitro clastogenic potency of these model mutagens is AD>CP>DMBA. Plateaus or reductions in micronucleus counts which may result from cytotoxicity and developmental arrest of spermatocytes with extensive chromosome aberrations were not observed at the mutagen doses studied.

EXAMPLE 2

In Vitro Dominant Lethal Assay

The overall experimental design entailed: (1) exposure of cultured Xenopus testis fragments to various concentrations of a test agent and a solvent control; (2) collection of sperm from the testis fragments at several different intervals over a 42 day culture period following exposure to the test agent; (3) fertilization of Xenopus eggs in vitro with the sperm collected from the cultured testis fragments; (4) quantitation of the percent of fertilized eggs which exhibit severe deformity or die between the first cleavage stage and the swimming tadpole stage.

There are several advantages of this in vitro dominant lethal assay relative to in vivo dominant lethal assays. First, since the testes are exposed directly to a specific concentration of the test agent, the dominant lethal frequency can be related to the test agent in a dosimetric manner. Second, unlike the mammal, early development in the frog is directly observable and relatively independent of nongenetic factors. Third, zygotes can be recognized unambiguously at the first cleavage stage, thus the dominant lethal frequency can be determined for all successful fertilizations. Fourth, motile sperm concentrations may be adjusted, if necessary, to assure that sufficient embryos are produced to avoid false negatives. Fifth, the necessity to sacrifice animals is limited to those relatively few males needed as a source of testicular material. Females serve only as a source of eggs and may thus be reused every 2–3 weeks.

Dominant lethal assays were performed by collecting sperm from testis fragments cultured 1, 10 and 35 days and determining the percent of eggs artificially fertilized by these sperm that failed to develop into normal swimming tadpoles, as described in detail earlier. Sperm recovered from testes cultured 1–35 days were indistinguishable from sperm collected from testes incubated only overnight, both with respect to fecundity and the percent normal embryonic development obtained (Risley et al. 1987, *Biol. Reprod.* 36:985–997).

Evaluation of a test agent's ability to induce dominant lethal mutations is conducted using similar methodology with the exception that testes are exposed to four different test concentrations and controls prior to culture, as described in Example 1. Sperm are collected from controls and test groups after 1, 7, 14, 21, 30, 37 and 44 days in culture. Most sperm present at each of these times are at the following stages of development during testis exposure to test agents: day 1, sperm; day 7, late spermatids; day 14, round spermatids; day 21, pachytene through secondary spermatocytes; day 30, zygotene spermatocytes; day 37, premeiotic S through leptotene; day 44, Type B spermatogonia to premeiotic S spermatocytes.

The dominant lethal frequency is determined from the average value for the 400–600 embryos in the duplicate test groups and is expressed as a percent of that in the concurrent controls, and statistical significance is evaluated by the t test. Only tests resulting in a doubling of the apparent lethality rate in concurrent controls at the 95% probability level are considered as conclusive positive results.

Unlike mammalian organisms, Xenopus does not have an epididymis. Sperm develop and are stored in the testes in the lumen of seminiferous lobules (analogous to seminiferous tubules) and in testicular ducts. Sperm that develop in cultured testis fragments are released into the lumen of the seminiferous lobules. The stage sensitivity of the dominant lethal assays is thus dependent upon the rate of replacement of "old" sperm by sperm which develop in vitro from earlier spermatogenic stages.

EXAMPLE 3

Sperm DNA Alkaline Elution Assays

The isolation of sperm used in the alkaline elution assays and the procedures for exposing and culturing testis fragments and collecting sperm at defined times is the same as described above in Example 2.

The alkaline elution assays are conducted essentially as described by Skare and Schrotel (1984, *Mutat. Res.* 130:283-294 and 295-303). However, unlike these reports, and those published by Sega et al. (1982, *Environ. Mutagen.* 4:347-348; 1986, *Mutat. Res.* 159:55-63), sperm is fractionated to obtain a preparation that is enriched for motile sperm and for those sperm actually capable of fertilizing eggs and passing the damaged DNA to the next generation. This approach enhances the correlation of dominant lethal and alkaline elution assays and increases the sensitivity of the alkaline elution assay to transmissable DNA damage in recently developed motile sperm. The sperm, collected in 3X F1, by the same procedure used in the dominant lethal assays is diluted with 2 volumes of distilled water (to induce active swimming) and then added to a 30 ml centrifuge tube containing sufficient Percoll to achieve a final Percoll concentration of 10%. The sperm suspension is covered with about 5 ml 1X F1 and allowed to stand for 15 mins, during which time active swimmers will enter the 1X F1 overlay. The sperm in this layer and the lower layer are then collected with a pipette and counted with a hemacytometer.

Sperm ($1 \times 10^6$) are loaded onto 2 μm polyvinyl chloride filters, lysed with SDS, and eluted with 20 mM EDTA, pH 12.1, as described (Sega and Owens, 1982, *Environ. Mutagen.* 4:347-348). The DNA eluted and remaining on the filters is assayed fluorimetrically using Hoechst 33258, the DNA specific fluorochrome. To estimate the relative frequency of interstrand cross-links, alkaline elution is conducted with and without prior X-irradiation of the sperm (Ewig and Kohn, 1978, *Cancer Res.* 38:3197-3203; Skare and Schrotel, 1984, *Mutat. Res.* 130:295-303). Crosslinking results in a retardation of the elution rate of X-irradiated sperm DNA. Protein-DNA crosslinking is estimated by comparison of the alkaline elution rate for sperm DNA lysed in SDS with and without proteinase K (Skare and Schrotel, 1984, *Mutat. Res.* 130:295-303; Kohn and Zwelling, 1982, *Dev. Oncol.* 10:86-96). One of the advantages of the use of Xenopus sperm in these assays is that, unlike mammalian sperm, reducing agents are not needed to remove protamines and Xenopus sperm proteins are readily solubilized in SDS.

EXAMPLE 4

Cytogenetic Analysis Of Spermatocyte Chromosomes

Cytogenetic analyses of chromosomes at meiotic metaphase I has been used to identify structural aberrations which occur in premeiotic S and meiotic prophase spermatocytes as they develop to the metaphase I stage in cultured testis fragments. The aberrations include: (1) multivalents resulting from nonhomologous chromosome interchanges. (2) univalents resulting from pre- or postsynaptic failure. (3) chromosome fragments and (4) chromatid breaks. Analyses of secondary spermatocyte chromosomes at metaphase II have been employed to identify numerical aberrations (aneuploidy) resulting from meiotic pre- or postsynaptic failure and nondisjunction of chromosomes at meiosis I.

Spermatocytes for cytogenetic analysis were recovered from cultured testis fragments using the collagenase dissociation and Percoll cell separation procedures described in detail in Example 1. To collect sufficient numbers of spermatocytes at metaphases I and II, cell division was blocked by adding colcemid (1 μg/ml) to culture media 12-14 hours prior to removal of testis fragments for dissociation. Colcemid (1 μg/ml) was also included in the collagenase and Percoll solutions.

Spermatocytes isolated from cultured testes were swollen by incubation in 0.06 M KCl (5 ml) for 30 minutes at room temperature and were then pelleted by centrifugation and fixed using 5 changes (5 ml each) of (4° C.) methanol:acetic acid (3:1 vol/vol). Chromosome spreads were prepared by procedures routine to those skilled in the art.

Duplicate slides were prepared for cells collected from each group of 10 testis fragments cultured for a specific time (1-30 days). Chromosome spreads on the slides were analyzed only if they were circular or ellipsoidal, well-spread, unitary metaphases. Slides were coded and analyzed blindly to avoid bias. With respect to metaphase II cells, only those with 18 (euploid) and 19 or 20 (hyperhaploid) chromosomes were counted since hypohaploidy may arise artefactually. The aneuploid frequency was estimated as 2 × hyperhaploid frequency.

A minimum of 100 spreads of metaphase I or II were analyzed. Statistical comparisons of intergroup aberration frequencies were accomplished with a two tailed t Test.

Evaluation of a test agent's ability to induce the chromosome aberrations described is conducted by preparing exposure and control groups of testis fragments as described earlier with the exception that each treatment group contains 10 testis fragments for each post-treatment culture period to be assayed (i.e. days 1, 3, 6, 9, 16, 23, 30 of post-treatment culture). Aberration frequencies at metaphases I and II are analyzed in both concurrent controls and test groups at each post-treatment time and are compared statistically to determine if the test agent induced specific or total aberrations. Unambiguous evidence for induction is obtained by demonstration of dose-dependency.

EXAMPLE 5

In Vitro Multi-Endpoint Assay for DNA Damage and Chromosome Aberrations Induced by Direct-Acting Genotoxic Chemicals in Developing Spermatogenic Cells and Sperm In this Example, several concurrent assays are conducted for genetic damage induced at different spermatogenic stages and surviving to the mature sperm stage. A schematic representation of the multi-endpoint assay protocol is presented below to show the variety of endpoints that may be assayed in the cells from the same test group of testis fragments.

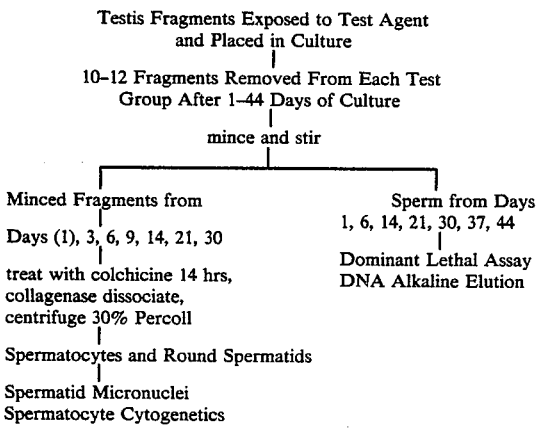

The assays are performed in at least two phases as shown in the following diagram.

PHASE I: IN VITRO DETECTION OF MALE GERM CELL GENOTOXICITY

In Phase I, several relatively rapid assays are used concurrently to scan the spermatogenic cycle for evidence of genetic damage induced as a result of exposure to several concentrations of a test agent. The dominant lethal and sperm DNA alkaline elution assays detect damage induced at any spermatogenic stage (particularly spermatids) and surviving to the mature sperm stage. Spermatid micronucleus assays are conducted to detect spermatogonial and meiotic chromosome breakage and missegregation. The spermatid assay may appear to be redundant with the dominant lethal assay, but it allows a determination of whether genetic damage is induced in prespermatid stages since such damage may not always survive in high frequency to the mature sperm stage. A comparison of the results for prespermatid genotoxicity with the results obtained from the sperm assays may also provide confirmation of the identification of the affected spermatogenic stages.

A positive, dose-dependent result from the Phase I assays may be followed by Phase II cytogenetic analyses of stored samples to obtain further characterization and confirmation of the genetic damage induced by a test agent. If genotoxicity is induced in spermatogonia or spermatocytes, cytogenetic analysis of spermatocytes in meiotic metaphase I and II may provide insights into types of chromosome rearrangements (i.e., translocations, univalency) that were induced prior to or during the meiotic divisions. The number of test samples that are actually analyzed cytogenetically is restricted to those cell types, test concentrations, and time points that show positive genotoxicity in the other assays. Phase II tests may be initiated at the first indication of positive Phase I results.

Methodological details for the spermatid micronucleus, dominant lethal, alkaline elution and spermatocyte cytogenetics assays have been described in Examples 1, 2, 3, and 4, respectively While the invention has been described in detail and with reference to specific embodiments thereof, it will be apparent to one skilled in the art that various changes and modifications can be made therein without departing from the spirit and scope thereof.

What is claimed is:

1. An in vitro screening test for identifying mutagenic and genotoxic agents during spermatogenesis, comprising:
   (1) Culturing Xenopus testis explants in vitro in the presence of at least one suspected mutagenic and/or genotoxic agent;
   (2) Separating said Xenopus testis explants from step (2) from said at least one suspected mutagenic and/or genotoxic agent;
   (3) Culturing said Xenopus testis explants from step (2) in the absence of said at least one suspected mutagenic and/or genotoxic agent such that spermatogonia in said Xenopus testis explants undergo spermatogenesis;
   (4) Isolating at least one type of spermatogenic cell at timed intervals during said step (3); and
   (5) Determining the mutagenic and/or genotoxic affect of said at least one suspected mutagenic and/or genotoxic agent.

2. The in vitro screening test as claimed in claim 1, wherein said testis explants are derived from *Xenopus laevis*.

3. The in vitro screening test as claimed in claim 1, wherein said step (4) comprises concurrently testing multiple genetic endpoints.

4. The in vitro screening test as claimed in claim 1, wherein said mutagenic and/or genotoxic affect is determined by conducting a dominant lethal assay.

5. The in vitro screening test as claimed in claim 1, wherein said mutagenic and/or genotoxic affect is determined by conducting a recessive lethal assay.

6. The in vitro screening test as claimed in claim 1, wherein said mutagenic and/or genotoxic affect is determined by conducting cytogenetics on chromosomes from spermatocytes in meiotic metaphases I and II.

7. The in vitro screening test as claimed in claim 1, wherein said mutagenic and/or genotoxic affect is determined by conducting an alkaline elution assay.

8. The in vitro screening test as claimed in claim 1, wherein said mutagenic and/or genotoxic affect is determined by conducting a micronucleus assay.

9. A serum-free media formulation for culturing Xenopus testis explants comprising one member selected from the group consisting of medium 1 and medium 2:

| Serum-Free Media Formulations (mg/L) |
|---|
| Medium 1: |

Serum-Free Media Formulations (mg/L)

| | | | |
|---|---|---|---|
| NaCl | 3786 | Proline | 60 |
| KCl | 186 | Serine | 240 |
| Na$_2$HPO$_4$.12H$_2$O | 358 | Threonine | 70 |
| CaCl$_2$.2H$_2$O | 147 | Tryptophan | 20 |
| MgCl$_2$.6H$_2$O | 102 | Tyrosine | 40 |
| MgSO$_4$.7H$_2$O | 123 | Valine | 60 |
| FeSO$_4$ | 0.834 | Glucose | 1000 |
| HEPES (pH 7.4) | 3576 | Oxaloacetate | 152 |
| Alanine | 130 | Sodium Pyruvate | 110 |
| Arginine-HCl | 140 | Bovine Serum Albumin (fatty acid-free) | 1000 |
| Aspartate-Mg | 450 | | |
| Cysteine-HCl.H$_2$O | 20 | Transferrin (human) | 10 |
| Cystine | 10 | Basal Medium Eagles Vitamin Mix | (1X) |
| Glutamate-HCl | 1200 | Ascorbate | 50 |
| Glutamine | 292 | DL-a-Tocopherol | 0.2 |
| Glycine | 60 | Retinol | 0.029 |
| Histidine-HCl.H$_2$O | 60 | Bovine Insulin (Zn) | 10 |
| Isoleucine | 50 | Dihydrotestosterone | 0.03 |
| Leucine | 80 | Testosterone | 0.03 |
| Lysine-HCl | 280 | Follicle-Stimulating Hormone | 5 |
| Methionine | 50 | Antibiotic-Antimycotic Mix (100 units/ml penicillin; 100 mcg/ml streptomycin sulfate; 0.25 mcg/ml Fungizone) | (1X) |
| Phenylalanine | 50 | | |

Medium 2:

Medium 1 - not containing tocopherol, ascorbate and testosterone, supplemented with linoleic acid (5 μg/ml).

10. A method for culturing Xenopus testis explants in vitro such that cells at all stages of a spermatogenic cycle are produced comprising culturing Xenopus testis fragments in one serum-free medium selected from the group consisting of medium 1 and medium 2:

Serum-Free Media Formulations (mg/L)

Medium 1:

| | | | |
|---|---|---|---|
| NaCl | 3786 | Proline | 60 |
| KCl | 186 | Serine | 240 |
| Na$_2$HPO$_4$.12H$_2$O | 358 | Threonine | 70 |
| CaCl$_2$.2H$_2$O | 147 | Tryptophan | 20 |
| MgCl$_2$.6H$_2$O | 102 | Tyrosine | 40 |
| MgSO$_4$.7H$_2$O | 123 | Valine | 60 |
| FeSO$_4$ | 0.834 | Glucose | 1000 |
| HEPES (pH 7.4) | 3576 | Oxaloacetate | 152 |
| Alanine | 130 | Sodium Pyruvate | 110 |
| Arginine-HCl | 140 | Bovine Serum Albumin (fatty acid-free) | 1000 |
| Aspartate-Mg | 450 | | |
| Cysteine-HCl.H$_2$O | 20 | Transferrin (human) | 10 |
| Cystine | 10 | Basal Medium Eagles Vitamin Mix | (1X) |
| Glutamate-HCl | 1200 | Ascorbate | 50 |
| Glutamine | 292 | DL-a-Tocopherol | 0.2 |
| Glycine | 60 | Retinol | 0.029 |
| Histidine-HCl.H$_2$O | 60 | Bovine Insulin (Zn) | 10 |
| Isoleucine | 50 | Dihydrotestosterone | 0.03 |
| Leucine | 80 | Testosterone | 0.03 |
| Lysine-HCl | 280 | Follicle-Stimulating Hormone | 5 |
| Methionine | 50 | Antibiotic-Antimycotic Mix (100 units/ml penicillin; 100 mcg/ml streptomycin sulfate; 0.25 mcg/ml Fungizone) | (1X) |
| Phenylalanine | 50 | | |

Medium 2:

Medium 1 - not containing tocopherol, ascorbate and testosterone, supplemented with linoleic acid (5 μg/ml).

under an atmosphere of air and at a temperature in a range of from about 20° to about 24° C.

11. The method for culturing Xenopus testis explants according to claim 10, wherein said culturing is conducted using a filter grid method.

12. The method for culturing Xenopus testis explants according to claim 10, wherein said culturing is conducted using a tissue culture flask method.

* * * * *